United States Patent [19]
Jayaraman

[11] Patent Number: 5,891,507
[45] Date of Patent: Apr. 6, 1999

[54] PROCESS FOR COATING A SURFACE OF A METALLIC STENT

[75] Inventor: Swaminathan Jayaraman, Bangalore, India

[73] Assignee: Iowa-India Investments Company Limited, Isle of Man

[21] Appl. No.: 901,362

[22] Filed: Jul. 28, 1997

[51] Int. Cl.[6] .............................. B05D 1/18; B05D 3/00

[52] U.S. Cl. ................ 427/2.25; 427/318; 427/377; 427/601

[58] Field of Search ................... 427/600, 601, 427/2.25, 2.28, 2.3, 318, 377

[56] References Cited

U.S. PATENT DOCUMENTS

| | | | |
|---|---|---|---|
| 3,849,185 | 11/1974 | Shepherd et al. | 427/395 |
| 4,353,934 | 10/1982 | Nakashima et al. | 427/601 |
| 5,143,750 | 9/1992 | Yamagata et al. | 427/601 |
| 5,222,971 | 6/1993 | Willard et al. | 606/158 |
| 5,330,500 | 7/1994 | Song | 606/198 |
| 5,441,516 | 8/1995 | Wang et al. | 606/198 |
| 5,458,905 | 10/1995 | Heagle | 427/2.12 |
| 5,460,859 | 10/1995 | Reale | 427/601 |
| 5,584,875 | 12/1996 | Duhamel et al. | 427/2.25 |
| 5,607,475 | 3/1997 | Cahalan et al. | 427/2.24 |
| 5,660,873 | 8/1997 | Nikolaychik et al. | 427/2.31 |
| 5,695,829 | 12/1997 | Quincy, III et al. | 427/601 |
| 5,721,131 | 2/1998 | Rudolph et al. | 435/240.243 |
| 5,735,872 | 4/1998 | Carpenter et al. | 606/198 |

*Primary Examiner*—Diana Dudash
*Attorney, Agent, or Firm*—Larson & Larson, P.A.; James E. Larson

[57] ABSTRACT

A metallic stent is coated with a synthetic or biological active or inactive agent that only adheres to the metallic surface of the stent and does not cover slots formed in the stent. In the method, a metallic stent is manufactured in a known manner and is then cleaned to remove surface contaminants and carbon deposits formed from cutting operations and electro-polishing procedures. The stent is then dried in a chamber in which nitrogen gas is purged and then placed in a bath containing a suitable surfactant, such as a long chain alkyl quaternary salt, that removes any residual carbon on the surface of the stent. The stent is then placed in a container filled with the coating agent and the container is placed in an ultrasonic bath. When the bath is activated, the stent swirls in the agent, which agent coats the stent but does not cover the slots of the stent. The stent is removed from the container and dried in a controlled atmosphere.

9 Claims, 2 Drawing Sheets

PROCESS FOR COATING A SURFACE OF A METALLIC STENT

BACKGROUND OF THE INVENTION

The present invention relates to a process for coating a surface of a metallic stent. In the prior art, it is known to coat a stent to protect the outer surface thereof and to make the stent inert to various biological processes that can occur when the stent is placed in the vascular system of a person. U.S. Pat. No. 5,330,500 to Song discloses a self-expanding endovascular stent with silicone coating. The Song stent is made of stainless steel wire formed into a closed zig-zag configuration. The frame is then wrapped in a mesh having a silicone coating thereon. The Song stent is typical of coated stents in that care has not been taken to preclude the coating agent from covering openings that are formed in the stent structures. The present invention overcomes the deficiencies of Song by providing a coated stent wherein the coating agent does not intrude into openings in the stent body that have been created for specific reasons.

SUMMARY OF THE INVENTION

The present invention relates to a process for coating a surface of a metallic stent. The inventive process includes the following steps:

(1) In the preferred embodiment, a metallic stent is manufactured in any suitable process. For example, a stent may be made using a laser cutting machine, a chemical etching machine, an electron beam cutting machine or any other device that manufactures a generally tubular stent having a plurality of slots formed through the surface thereof.

(2) After the stent has been so manufactured, the stent is electro-polished to remove any burrs or other surface irregularities that could damage a patient in whom the stent is to be implanted.

(3) After electro-polishing the stent, cleaning procedures are undertaken to remove surface contaminants and carbon deposits resulting from the cutting operations and electro-polishing. The stent is first placed in a bath of deionized water and is heated to boiling temperature for approximately one-half hour. The stent is then removed from the bath and is dried in a chamber for about twelve hours with the chamber being purged of any nitrogen gas.

(4) Thereafter, the stent is placed in a bath containing a suitable surfactant such as, for example, a long chain alkyl quaternary salt such as those obtained by reacting dodecyl-chloride with tridodecylamine. Alternatively, other salts may be employed that are suitable for use with high carbon solvents. These surfactants remove all residual carbon present on the stent surfaces.

(5) After the steps described above have been completed, the stent may be coated with an agent that is either synthetic or biological, active or inactive. Active agents include heparin and other anticoagulants, EDGF (endothelium derived growth factor), VGFs (vascular growth factors) or inactive agents like silicone, polyurethane, PTFE (polytetrafluoroethylene) and/or other polymers. Inactive (or inert) agents may have active agents such as those listed above encapsulated there within.

(6) In the coating process, the coating agent, whichever one is chosen, is placed in a suitable container such as, for example, a glass beaker. The container is placed in an ultrasonic bath that is filled with a liquid such as, for example, water or alcohol. When the ultrasonic bath is activated, the container sonicates. When the stent is placed inside the beaker filled with the coating agent, the stent swirls within the coating agent in a continuous fashion with the swirling being attributable to the ultrasonic energy that is passed from the liquid in the ultrasonic bath onto the coating agent within the container and thereafter into the stent. This energy transfer enables the coating agent to fill the surface crevices of the stent and form a uniform layer of coating while preventing the coating agent from filling the slots of the stent. If desired, a plurality of stents may be simultaneously subjected to the inventive process including placement of a plurality of such stents within the container to be subjected to ultrasonic energy.

(7) Thereafter, the stent is removed from the container and is dried in a controlled atmosphere.

As such, it is a first object of the present invention to provide a process for coating a surface of a metallic stent.

It is a further object of the present invention to provide such a process wherein the stent is coated but slots thereof are left open.

It is a yet further object of the present invention to provide such a process wherein the coating agent may be active or inactive.

It is a yet further object of the present invention to provide such a process that employs the use of ultrasonic energy to assure a uniform and complete coating.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 4:
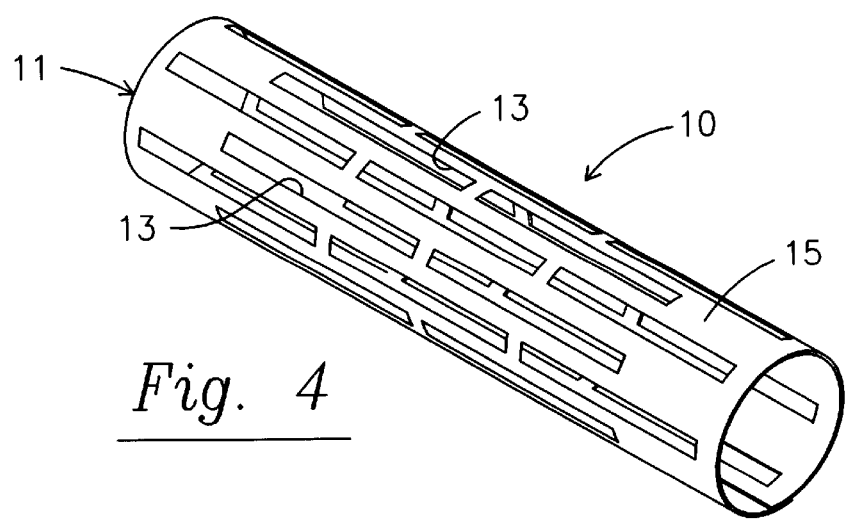
FIG. 4 shows a stent coated in accordance with the teachings of the present invention.

With reference, first, to FIG. 4, a stent is generally designated by the reference numeral 10 and is seen to include a tubular body 11 having a plurality of slots 13 formed completely through the body. A coating 15 is formed on the inner and outer surface of the body 11 and, as seen in FIG. 4, the coating does not cover the slots 13.

Figure 1:
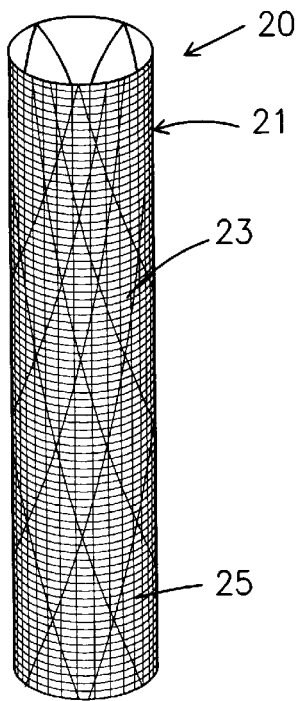
FIG. 1 shows a stent coated in accordance with the teachings of the invention disclosed in U.S. Pat. No. 5,330,500 to Song.

By comparison with FIG. 4, FIG. 1 shows a stent 20 having a body 21 including slots 23 and a coating 25 formed thereon in accordance with the teachings of U.S. Pat. No. 5,330,500 to Song. As seen in FIG. 1, the coating 25 covers the slots 23 and obstructs them.

As is well known, stents are provided with slots or other openings because such slots or other openings are instrumental in facilitating the retention of a stent in its position of placement within the vascular system of the human body. The slots or other openings allow tissues to grow and/or protrude therethrough to facilitate firm fixation of an implanted stent. Obscuring or covering of the slots or other openings of a stent during a coating process creates a great risk of failure of a stent implantation operation.

In accordance with the teachings of the inventive process, a stent may be reliably coated without obscuring of the slots or other openings thereof.

As is well known, stents may be made through fabrication of a tubular form that is then subjected to the process of a laser cutting machine, a chemical etching machine, an electron beam cutting machine or other device designed to cut slots or other openings therethrough such as the openings 13 seen in FIG. 4. After the process has been completed, the surfaces of the stent may have surface irregularities such as burrs, nicks, rough edges and the like that could damage body tissues during the implantation process and thereafter. Thus, after a stent has been manufactured in the manner described above, it is customary to electro-polish the stent or polish it using some other suitable procedure to remove any such surface irregularities.

In accordance with the teachings of the present invention, after the stent has been suitably polished, it is placed in a bath of deionized water. The water is then heated to boiling temperature and the stent is retained therein for from fifteen minutes to forty-five minutes. Thereafter, the stent is removed from the bath and placed in a sealed chamber in which nitrogen gas is purged. The chamber is kept at a temperature within the range of 40° C. to 80° C. and at a pressure in the range of 2 psi to 14 psi. This drying step is carried out for a period of eight to twelve hours.

Thereafter, the stent is removed from the sealed chamber and placed in a bath containing a suitable surfactant that is intended to remove all residual carbon that might still be present on the stent surfaces. Applicant has found that surfactants suitable for use in this process step consist of long chain alkyl quaternary salts such as tridodecylammonium chloride obtained by reacting dodecychloride with tridodecylamine. Other salts may suitably be employed that contain high carbon solvents. Again, this step is included to best facilitate removal of any and all residual carbon that might still be present on the stent surfaces.

Figure 2:
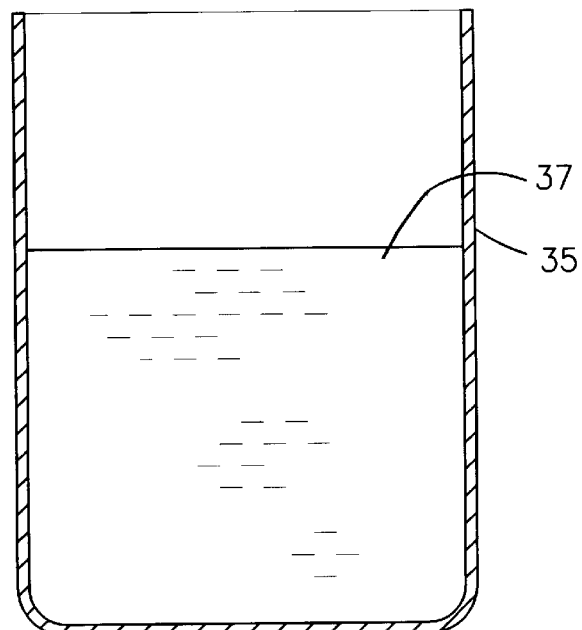
FIG. 2 shows a schematic representation of an ultrasonic bath.
Figure 2:
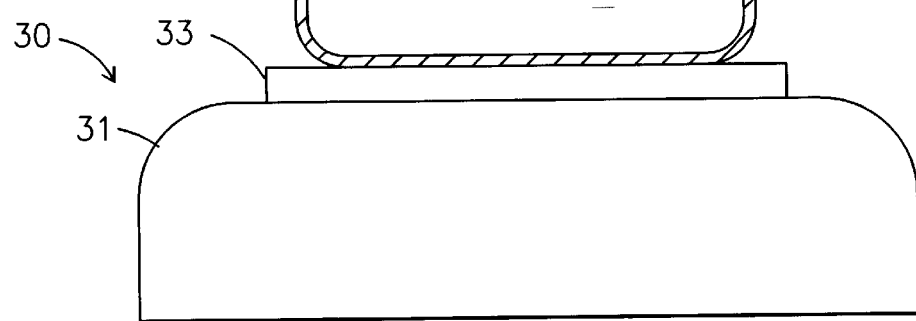

With reference to FIG. 2, an ultrasonic bath is generally designated by the reference numeral 30 and is seen to include a housing 31 having a surface 33 on which a bath chamber 35 is mounted. A liquid 37 such as water or alcohol fills the container 35. Within the housing 31, an ultrasonic generator (not shown) is contained and is designed to impart ultrasonic energy to the liquid 37 within the container 35. Such an ultrasonic generator is well known to those skilled in the art.

The next process step in the inventive process involves coating the stent 10 by immersing it in a coating material exposed to ultrasonic energy. In this regard, reference is made to FIG. 3 that shows a container 39 filled with coating agent 41 and with the stent 10 immersed therein.

Various coating agents may be employed using the inventive process. Such coating agents may be synthetic or biological, active or inactive. Active agents include heparin and other anticoagulants, EDGF (endothelium derived growth factor) or VGFs (vascular growth factors). Inactive agents (inert agents) may include silicon, polyurethane, PTFE (polytetrafluoroethylene) and/or other polymers. If desired, such inactive or inert agents may have active agents such as those listed above encapsulated there within.

Figure 3:
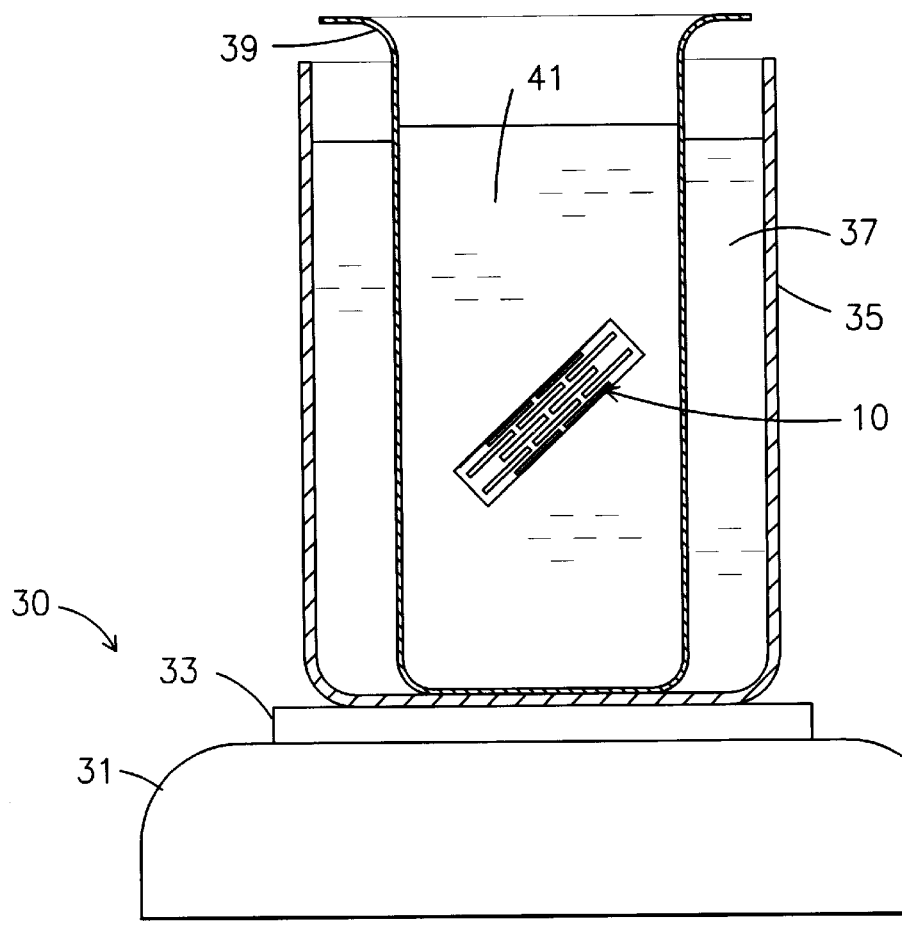
FIG. 3 shows the ultrasonic bath of FIG. 2 with a container filled with coating material and a stent therein being coated.

With reference to FIG. 3, the coating agent 41 is placed within the container 39. The stent 10 is placed within the container 39 immersed within the coating agent 41. The ultrasonic generator is activated and causes the container 39 to "sonicate". Sonication of the container 39 causes the stent 10 to swirl within the coating agent 41, which swirling action is attributable to ultrasonic energy that is passed from the liquid 37 within the container 35 and thence into the container 39 and the coating agent 41. This action causes molecules of the coating agent to fill any and all surface crevices within the surface of the stent 10 to form a uniform coating layer while also, concurrently, preventing the coating agent from covering the slots 13 formed through the surface thereof.

After a prescribed period of time, within the range of two to ten minutes, the stent 10 is removed from the container 39 and is suitably dried in a controlled atmosphere.

In this way, a stent may be coated in a manner that precludes covering of the slots or other surface openings thereof so that the stent 10 may be suitably implanted in the vascular system of a human being while retaining its full intended function.

Accordingly, an invention has been disclosed in terms of a preferred process for coating a surface of a metallic stent of great novelty and utility.

Of course, various changes, modifications and alterations in the teachings of the inventive method may be contemplated by those skilled in the art without departing from the intended spirit and scope thereof.

As such, it is intended that the present invention only be limited by the terms of the appended claims.

I claim:

1. A process for coating a surface of a stent, the stent having a plurality of longitudinal openings therethrough, the process including the steps of:
   a) immersing said stent within a coating agent in a container;
   b) placing the container in an ultrasonic bath and subjecting said stent and coating agent within the container to ultrasonic energy;
   c) said stent swirling within said coating agent when subjected to ultrasonic energy, said stent being coated with said coating agent with said longitudinal openings left uncoated.

2. The process of claim 1, wherein said coating agent is selected from the group consisting of heparin, EDGF and VGFs.

3. The process of claim 1, wherein said coating agent is selected from the group consisting of silicone, polyurethane and polytetrafluoroethylene.

4. The process of claim 1, further including the step, prior to said immersing step, of placing said stent in a bath of deionized water and boiling said water for twenty minutes to forty-five minutes.

5. The process of claim 4, wherein, after said placing and boiling steps, including the step of drying said stent in a nitrogen-purged atmosphere for eight to twelve hours.

6. The process of claim 5, further including the step, after said drying step, of bathing said stent in a surfactant.

7. The process of claim 6, wherein said surfactant comprises a long chain alkyl quaternary salt of at least 12 C atoms.

8. The process of claim 1, prior to said immersing step, including the step of electro-polishing said stent.

9. A process for coating a surface of a stent, the stent having a plurality of openings therethrough, the process including the steps of:
   a) electro-polishing said stent;
   b) placing said stent in a bath of deionized water and boiling said water for twenty minutes to forty-five minutes;

c) drying said stent in a nitrogen-purged atmosphere for eight to twelve hours;

d) bathing said stent in a surfactant comprising a long chain alkyl quaternary salt of at least 12 C atoms;

e) immersing said stent within a coating agent selected from the group consisting of heparin, EDGF, VGFs, silicone, polyurethane and polytetrafluoroethylene;

f) subjecting said stent and coating agent to ultrasonic energy, said stent swirling within said coating agent and being coated with said coating agent with said openings left uncoated; and g) drying said stent in a controlled atmosphere.

* * * * *